United States Patent [19]

Morikawa et al.

[11] Patent Number: 5,840,546
[45] Date of Patent: Nov. 24, 1998

[54] **KERATIN SULFATE HYDROLASE OBTAINABLE BY USING *BACILLUS CIRCULANS* AND METHOD FOR PRODUCING SAME**

[75] Inventors: Kiyoshi Morikawa, Tokyo; Hiroshi Maruyama, Akiruno; Takako Isomura, Koganei; Kiyoshi Suzuki, Tachikawa; Sadao Tatebayashi, Akiruno, all of Japan

[73] Assignee: Seikagaku Corporation, Tokyo, Japan

[21] Appl. No.: 849,637

[22] PCT Filed: Nov. 22, 1995

[86] PCT No.: PCT/JP95/02385

§ 371 Date: May 22, 1997

§ 102(e) Date: May 22, 1997

[87] PCT Pub. No.: WO96/16166

PCT Pub. Date: May 30, 1996

[30] Foreign Application Priority Data

Nov. 22, 1994 [JP] Japan ................................. 6-288031

[51] Int. Cl.$^6$ ............................. C12P 21/04; C12N 9/24; C12N 9/26
[52] U.S. Cl. ........................ 435/71.1; 435/200; 435/201
[58] Field of Search ................................ 435/200, 71.1, 435/201

[56] References Cited

U.S. PATENT DOCUMENTS 5,290,695 3/1994 Morikawa et al. .................. 435/232

FOREIGN PATENT DOCUMENTS 02057182 2/1990 Japan .

OTHER PUBLICATIONS

Takegawa et al. (1991) Eur J Biochem, 202 (1), "Complete Amino Acid Sequence of Endo-β –N–Acetylglucosaminidase from Flavobacterium–sp.", pp. 175–180.

Maeno et al. (1992) J. Histochem. Cytochem., 40(11), "Nature and Distribution of Mineral–binding, KeratanSulfate–containing Glycoconjugates in Rat and Rabbit Bone", pp. 1779–1788.

Watanabe et al. (1992) J. Bacteriol., 174(2), "Structure of the Gene Encoding Chitinase D of *Bacillus Circulans* WI–12 and Possible Homology of the Enzyme to Other Prokaryotic Chitinases and Class III PLant Chitinases", pp. 408–414.

Watanabe et al. (1993) J. Biol. Chem., 268 (25), "Identification of Glutamic Acid 204 and Aspartic Acid 200 in Chitinase A1 of *Bacillus Circulans* WI–12 as Essential Residues for Chitinase Activity", pp. 18567–18572.

Nakazawa (1989) in Keratan Sulphate: Chemistry, Biology and Chemical Pathology (Greiling, H., and Scott, J.E., Eds.) "Substrate Specificity of Keratan Sulphate Degrading Enzymes (Endo–β–Galactosidase, Keratanase and Keratanase II) from Microorganisms", pp. 99–110. The Biochemical Society, London.

Angata et al. (1994) Glycobiology, 4(4), "Identification, Developmental Expression and Tissue Distribution of Deaminoneuraminate Hydrolase (Kdnase) Activity in Rainbow Trout", pp. 517–523.

*Primary Examiner*—Jon P. Weber
*Attorney, Agent, or Firm*—Knobbe, Martens, Olson & Bear, LLP

[57] ABSTRACT

A keratan sulfate hydrolase of an endo-β-N-acetylglucosaminidase type, obtained by culturing *Bacillus circulans* such as *Bacillus circulans* KsT202, has reactivity on keratan polysulfate at high concentrations, an optimum pH of 4.5–6, stability at a pH of 6–7, an optimum temperature of 50°–60° C., thermostability at a temperature of 45° C., and a molecular weight of approximately 200,000 dalton.

8 Claims, 7 Drawing Sheets

10% Keratan polysulfate solution, 37°C, 24 hr

KERATIN SULFATE HYDROLASE OBTAINABLE BY USING *BACILLUS CIRCULANS* AND METHOD FOR PRODUCING SAME

TECHNICAL FIELD

The present invention relates to a novel keratan sulfate hydrolase, a method for producing the same, and a novel microorganism producing the same.

BACKGROUND ART

As enzymes derived from microorganisms which hydrolyze keratan sulfate (hereinafter referred to as a keratan sulfate hydrolase), an endo-β-galactosidase type enzyme which hydrolyzes galactosidic linkages in the sugar chain of keratan sulfate and an endo-β-N-acetylglucosaminidase type enzyme which hydrolyzes N-acetylglucosaminidic linkages of that are known.

As microorganisms producing the endo-β-N-acetylglucosaminidase type enzyme, only Ks 36 strain belonging to the genus Bacillus, which has been isolated from soil samples by the present inventors, is known, and the microbiological characteristics and enzymological properties thereof have been clarified (Japanese Patent Application Laid-open No. 2-57182).

Keratan sulfate is grouped into keratan sulfate I which exists in corneas of animals, and keratan sulfate II and keratan polysulfate which are contained in the tissues such as cartilages, and each of them is a copolymer comprising the disaccharide of galactose and N-acetylglucosamine as a constitutional unit. In the former, most of the 6-positions of N-acetylglucosamine have a hydroxyl group, while a large proportion of the constituents are the disaccharide disulfate of which both hydroxyl groups of the 6-positions of N-acetylglucosamine and galactose are sulfated in the latter.

A keratan sulfate hydrolase of endo-β-N-acetylglucosaminidase type acts on these keratan sulfates above and mainly produces sulfated keratan sulfate disaccharide and sulfated keratan sulfate tetrasaccharide as the hydrolyzates. The disaccharide includes monosulfated keratan sulfate disaccharide and disulfated keratan sulfate disaccharide whose reducing end sugars are N-acetylglucosamine.

Accordingly, the hydrolyzates of keratan sulfate by the keratan sulfate hydrolase of endo-β-N-acetylglucosaminidase type are mainly sulfated keratan sulfate disaccharide and sulfated keratan sulfate tetrasaccharide having the N-acetyllactosamine structure.

N-acetyllactosamine is contained in the sugar chain of oligosaccharide in human milk, lipopolysaccharides, and a variety of glycoproteins and glycolipid, known as a growth factor of *Lactobacillus bifidus* (*Bifidus* factor) which is an enterobacterium of breast-fed babies, and promisingly expected to be used for high nutritious foods such as prepared dried milk for babies. And recently, the oligosaccharide represented by the so-called sialyl Le$^x$ sugar chain which is produced by bonding fucose to the N-acetylglucosamine residue of N-acetyllactosamine by the α-1,3 bond and sialic acid to the galactose residue by the α-2,3 bond, has an inhibitory activity to cell adhesion and is expected to be a constituent of anti-inflammatory agents, and therefore N-acetyllactosamine is promisingly expected also as a starting material of the sialyl Le$^x$ sugar chain synthesis.

It is known that N-acetyllactosamine is prepared by a method of synthesis with an enzyme, a method of desulfation of sulfated keratan disaccharide which is a hydrolyzate with a keratan sulfate hydrolase, and so on. And it is known that sulfated N-acetyllactosamine tetrasaccharide is prepared by hydrolyzing keratan sulfate with a keratan sulfate hydrolase as described above. However, as the keratan sulfate hydrolase of endo-β-N-acetylglucosaminidase type used in the preparation above, only the keratan sulfate hydrolase (keratan sulfate hydrolase II) derived from the Ks 36 strain is known as described above. This enzyme does not have enough thermostability as it is not stable at approximately 30° C. or above; therefore, it is not considered an appropriate enzyme in order to prepare sulfated keratan sulfate disaccharide or tetrasaccharide on a large industrial scale. Especially in the preparation of sulfated keratan sulfate disaccharide or tetrasaccharide by a batch degradation method or immobilized enzyme degradation methods, the keratan sulfate hydrolase is required to have high thermostability, and the development of the keratan sulfate hydrolase of endo-β-N-acetylglucosaminidase type having high thermostability has been desired.

DISCLOSURE OF THE INVENTION

The present invention has been made considering the viewpoint as described above, an object of which is to provide a novel keratan sulfate hydrolase of endo-β-N-acetylglucosaminidase type having high thermostability, a novel microorganism producing the same, and a method for producing the same.

The present inventors widely investigated soil microorganisms in order to obtain a microorganism producing a keratan sulfate hydrolase of endo-β-N-acetylglucosaminidase type having high thermostability, and have succeeded in isolating a strain of *Bacillus circulans* from the soil in Saitama Prefecture in Japan which meet a desired purpose. Though the keratan sulfate hydrolase produced by the strain has similar functions to the conventional keratan sulfate hydrolase II, there are differences in thermostability (it is stable up to 45° C.) and other enzymological properties. Therefore, it has been confirmed that it is an extremely characteristic enzyme. Thus the present invention has been completed.

Namely, a keratan sulfate hydrolase of the present invention (hereinafter sometimes referred to as "the present enzyme" or "the enzyme of the present invention") is a novel enzyme having the following physical and chemical properties:

(1) action:
the present enzyme acts on keratan sulfate, and hydrolyzes the N-acetylglucosaminidic linkage thereof;

(2) substrate specificity:
the present enzyme acts on keratan sulfate I, keratan sulfate II, and keratan polysulfate, and produces sulfated keratan sulfate disaccharide and sulfated keratan sulfate tetrasaccharide as the main hydrolyzates;

(3) optimum reaction pH:
the present enzyme has an optimum reaction pH from 4.5 to 6 in the 0.1M acetate buffer or 10 mM tris-acetate buffer, at 37° C.;

(4) pH stability:
the present enzyme has a pH stability from 6 to 7 when the present enzyme is stood in the 0.1M acetate buffer or 10 mM tris-acetate buffer, at 37° C., for one hour;

(5) optimum reaction temperature:
the present enzyme has an optimum reaction temperature from 50°0 to 60° C. when the present enzyme reacts in the 0.1M acetate buffer, pH 6.0, for 10 minutes;

(6) thermostability:

the present enzyme is at least stable at 45° C. or less when the present enzyme is stood in the 0.1M acetate buffer, pH 6.0, for one hour.

The keratan sulfate hydrolase having the properties described above can be produced by *Bacillus circulans*.

Further, a method for pruducing the keratan sulfate hydrolase of the present invention is characterized by culturing a microorganism which belongs to the genus Bacillus and has the ability to produce the keratan sulfate hydrolase of the present invention in a medium, and recovering the keratan sulfate hydrolase from the medium and/or microbial cells.

The microorganism belonging to the genus Bacillus used in this method is preferably *Bacillus circulans*. Further, the keratan sulfate hydrolase from the microbial cells is recovered preferably from the extract of the microbial cells which is prepared by lysing or disrupting the microbial cells to obtain an extract of the microbial cells and treating the extract with deoxyribonuclease.

A strain of *Bacillus circulans* of the present invention belongs to the genus Bacillus and has the ability to produce the keratan sulfate hydrolase having the properties described above. An example of the strain of *Bacillus circulans* includes *Bacillus circulans* KsT202.

The present invention will be described in detail below.

(1) Novel strain producing the keratan sulfate hydrolase of the present invention The enzyme of the present invention may be produced by a microorganism belonging to the genus Bacillus. The microorganism belonging to the genus Bacillus used in the present invention is not especially limited so long as the microorganism belonging to the genus Bacillus has the ability to produce the enzyme of the present invention; however, *Bacillus circulans*, especially *Bacillus circulans* KsT202 is preferably used. This strain is a novel one which has been isolated by the present inventors from the soil obtained in Saitama Prefecture, and has been identified as *Bacillus circulans* because of it's microbiological properties as described in the examples below. The present strain assimilates keratan sulfate, while none of the known *Bacillus circulans* has been reported to assimilate keratan sulfate so far, and therefore, the present strain is a novel one which is distinguishable from known ones in this regard, and it is named KsT202. Accordingly, the strain of *Bacillus circulans* producing the keratan sulfate hydrolase of the present invention is novel itself, and the present invention includes a strain of *Bacillus circulans* producing the keratan sulfate hydrolase of the present invention which has the properties described above, without limiting to the present strain.

The microorganism producing the keratan sulfate hydrolase may be obtained as follows. A small amount of a material for isolation such as soil is added to a liquid medium containing nitrogen sources, inorganic salts, and keratan sulfate, and cultured for a few days. Then the supernatant of the cultured medium is spotted on a filter paper and the liquid medium (control) is also spotted there in the same way. After air-drying, the filter paper is soaked in a toluidine blue solution and washed adequately with a dilute acetic acid solution, and the color on the spotted site of the supernatant of the cultured medium is compared with that of the control. Since toluidine blue combines with keratan sulfate to develop a blue color, it can be confirmed that a keratan sulfate assimilative microorganism exists in the sample which develops a less color than the control. The keratan sulfate assimilative microorganism is pure-isolated by a conventional method from the liquid medium containing the keratan sulfate assimilative microorganism using a plate medium (e.g., Heart infusion Agar). Through a variety of the microorganisms which have been pure-isolated are examined for the assimilation of keratan sulfate using a liquid medium in the same manner as in the above, the desired keratan sulfate assimilative microorganism can be obtained.

The *Bacillus circulans* KsT202 isolated as described above had been deposited in National Institute of Bioscience and Human-Technology of Agency of Industrial Science and Technology of Ministry of International Trade and Industry (1-3, Higashi 1-chome, Tsukuba-shi, Ibaraki-ken 305, Japan) on Sep. 5, 1994 under accession number FERM P-14516, and then it was transferred to the international deposition based on Budapest treaty on Nov. 6, 1995, and has been deposited under accession number FERM BP-5285.

(2) Keratan sulfate hydrolase of the present invention

The keratan sulfate hydrolase of the present invention is produced and accumulated in the medium or microbial cells by culturing a microorganism belonging to the genus Bacillus which has the ability to produce a keratan sulfate hydrolase, e.g., *Bacillus circulans* KsT202, in a nutrient medium usually used for cultures of microorganisms, preferably in a medium containing keratan sulfate or a substance including it, in order to enhance the ability to produce the enzyme, and the enzyme may be recovered by a conventional method.

The method for producing the present enzyme is further described using *Bacillus circulans* KsT202 as an example. *Bacillus circulans* KsT202 is cultured in a proper nutrient medium, e.g., a medium containing proper carbon sources, nitrogen sources, inorganic salts, and keratan sulfate, or substances including them, and the like, so as to produce and accumulate the present enzyme in the medium or the microbial cells. As the carbon source, every substance can be used so far as it can be metabolizable, for example, D-glucose, L-arabinose, D-xylose, D-mannose, starch, and a variety of peptones. The nitrogen source usable includes organic or inorganic nitrogen compounds or substances containing them, for example, yeast extract, malt extract, a variety of peptones, a variety of broth extract, corn steep liquor, amino acid solutions, ammonium salts, and the like. The inorganic salts which can be added to the medium include a variety of phosphates, salts of magnesium, potassium, sodium, calcium, etc. If necessary, a variety of inorganic or organic substances which are required to grow the microorganism or produce the enzyme, for example, antiforming agents such as silicone oil, sesame oil, and a variety of surfactants, and vitamins can be added to the medium.

According to the present invention, by adding keratan sulfate or a substance containing it as an inducer of the present enzyme, the present enzyme can be produced in a larger amount. The inducer may be added at the beginning or in the course of the culture. Usually, keratan sulfate is added to adjust the concentration thereof to the range of from 0.2 to 2% in order to obtain desirable results.

The culture may be carried out in the form of liquid culture or solid culture, and usually liquid culture is preferable. Submerged aeration culture with agitation is industrially advantageous. The culture conditions in the present invention may be selected and adjusted appropriately so as to produce the present enzyme most advantageously. The culture temperature may vary from 30° to 45° C., preferably from 35° to 45° C. The culture period is usually about 8 to 24 hours depending upon the other culture conditions, and the culture may be stopped when the maximal accumulation of the present enzyme is achieved. The pH of the medium is around neutral in preparing the medium, and no special adjustment is generally required.

The enzyme of the present invention may be recovered both from the supernatant of the cultured medium and the microbial cells thus obtained. The enzyme in the microbial cells can be recovered as an extract of the microbial cells by disrupting or lysing the microbial cells by means of an ultrasonic-disrupting method, osmotic shock, lysing method using a nonionic surfactant such as polyoxyethylene(23) lauryl alcohol ether(Brij-35) and the like, freeze-thawing of microbial cells, lysing method using a lytic enzyme such as lysozyme, or the combination thereof. Furthermore, the extract of the microbial cells is treated with deoxyribonuclease and the like to increase the recovery from the extract of the microbial cells and elevate the amount of the extracted enzyme. This effect is significant especially in the bacteriolysis using a bacteriolytic enzyme. And when using the surfactant, the extraction efficiency rises but the salting out with ammonium sulfate afterwards sometimes will become difficult.

The keratan sulfate hydrolase in the supernatant of the culture medium or the extract of the microbial cells may be purified by adding ammonium sulfate to them to 70% saturation, then dialyzing the precipitate deposited, and subjecting the dialysate to chromatography using an ionexchanger, gel filtration support, hydrophobic support, or the like.

For example, the activity of the enzyme of the present invention may be determined by measuring an increase of the reducing end produced by hydrolyzing keratan sulfate by the Park-Johnson method (J. Biol. Chem., 181, 149, (1949)). Namely, 10 $\mu$l of the enzyme solution and 180 $\mu$l of 0.1M acetate buffer (pH 6.0) are added to 10 $\mu$l of a solution containing keratan polysulfate (10 mg/ml) derived from cartilage of sharks, and the mixture is allowed to react at 37° C. for 10 minutes. The reaction is stopped by adding 200 $\mu$l of the carbonate-cyanide solution of the Park-Johnson method. Then 200 $\mu$l of the ferricyanide solution is added, and the reaction solution is heated in a boiling-water bath for 15 minutes and cooled in a water bath. And then, 1 ml of the iron (III) solution is added thereto and mixed. After 15 minutes, the absorbance is determined at 690 nm. The absorbance at this time is defined as A, the initial absorbance of the same reaction solution (zero minute of the reaction period) is defined as $A_0$, and the absorbance when using 200 $\mu$l of a galactose solution (10 $\mu$g/ml) as the standard instead of the reaction solution and treating in the same manner is defined as $A_{st}$.

One unit of the enzyme quantity (hereinafter sometimes referred to as Units or U) which produces the reducing end corresponding to 1 $\mu$mole of galactose in a minute under the conditions above is calculated from the following equation.

$$1 \text{ unit/ml} = (A - A_0)/A_{st} \times \underset{\text{(Mole correction)}}{2/180.161} \times$$

$$\underset{\text{(Dilution correction)}}{1000/10} \times \underset{\text{(Time correction)}}{1/10}$$

$$= (A - A_0)/A_{st} \times 0.111$$

Next, the physical and chemical properties of the novel keratan sulfate hydrolase of the present invention will be described below.

(1) Action

The present enzyme acts on keratan sulfate and hydrolyzes the N-acetylglucosaminidic linkage thereof.

(2) Substrate specificity

The present enzyme acts on keratan sulfate I, keratan sulfate II, and keratan polysulfate and produces sulfated keratan sulfate disaccharide and sulfated keratan sulfate tetrasaccharide as the main hydrolyzates (see FIG. 1).

Further, it is confirmed that the present enzyme produces sulfated keratan sulfate pentasaccharide also as a hydrolyzate.

The present enzyme does not act on desulfated keratan, and requires a sulfate group in the sugar chain at the action site. The present enzyme does not act on glycosaminoglycan other than keratan sulfate.

The present enzyme acts on keratan polysulfate even in a solution of high concentration (10%) (see FIG. 2).

(3) Optimum reation pH

The present enzyme has an optimum reation pH from 4.5 to 6, which is determined in the 0.1M acetate buffer or 10 mM tris-acetate buffer at 37° C. (see FIG. 3).

(4) pH Stability

The present enzyme has a pH stability around 6 to 7, which is determined when standing in the 0.1M acetate buffer or 10 mM tris-acetate buffer for one hour at 37° C. (see FIG. 4).

(5) Optimum reaction temperature

The present enzyme has an optimum reaction temperature from 50° to 60° C. which is determined by the reaction in the 0.1M acetate buffer (pH 6.0) at from 37° to 65° C. for 10 minutes (see FIG. 5).

(6) Thermostability

The present enzyme is not deactivated at 45° C. and has 65% of the residual activity at 50° C. when the residual activity of it is determined after heating at from 30° to 55° C. in the 0.1M acetate buffer (pH 6.0) for one hour (see FIG. 6).

(7) Molecular weight

When the present enzyme is electrophoresed by SDS-polyacrylamide gel electrophoresis (in the gel concentration of 7%) under the reducing and non-reducing conditions, a single band having the same mobility is observed under the both conditions and molecular weight of the present enzyme is calculated approximately 200,000 dalton from the calibration curve of the standard protein (see FIG. 7).

(8) Inhibition

There is no inhibition when the activity of the present enzyme is determined in the presence of a variety of agents described below in the final concentration of 1 mM.

$Na^+$, $K^+$, $Mn^{2+}$, $Mg^{2+}$, $Co^{2+}$, $Ba^{2+}$, $Ca^{2+}$, $Zn^{2+}$, $SO_4^{2-}$, $PO_4^{3-}$, EDTA (ethylenediaminetetraacetic acid), and PCMB (p-chloromercuribenzoic acid).

By comparing the results described above with the keratan sulfate hydrolase II (Japanese Patent Application Laid-open No. 2-57182) which is a known keratan sulfate hydrolase of endo-$\beta$-N-acetylglucosaminidase type, it is confirmed that the enzyme of the present invention is a novel one having different properties from the known enzyme, since there are differences in reactivity on keratan polysulfate at high concentrations, optimum pH, pH stability, optimum temperature, thermostability, influence of inhibition by agents, and the like.

PREFERRED EMBODIMENTS FOR CARRYING OUT THE INVENTION

Figure 1:
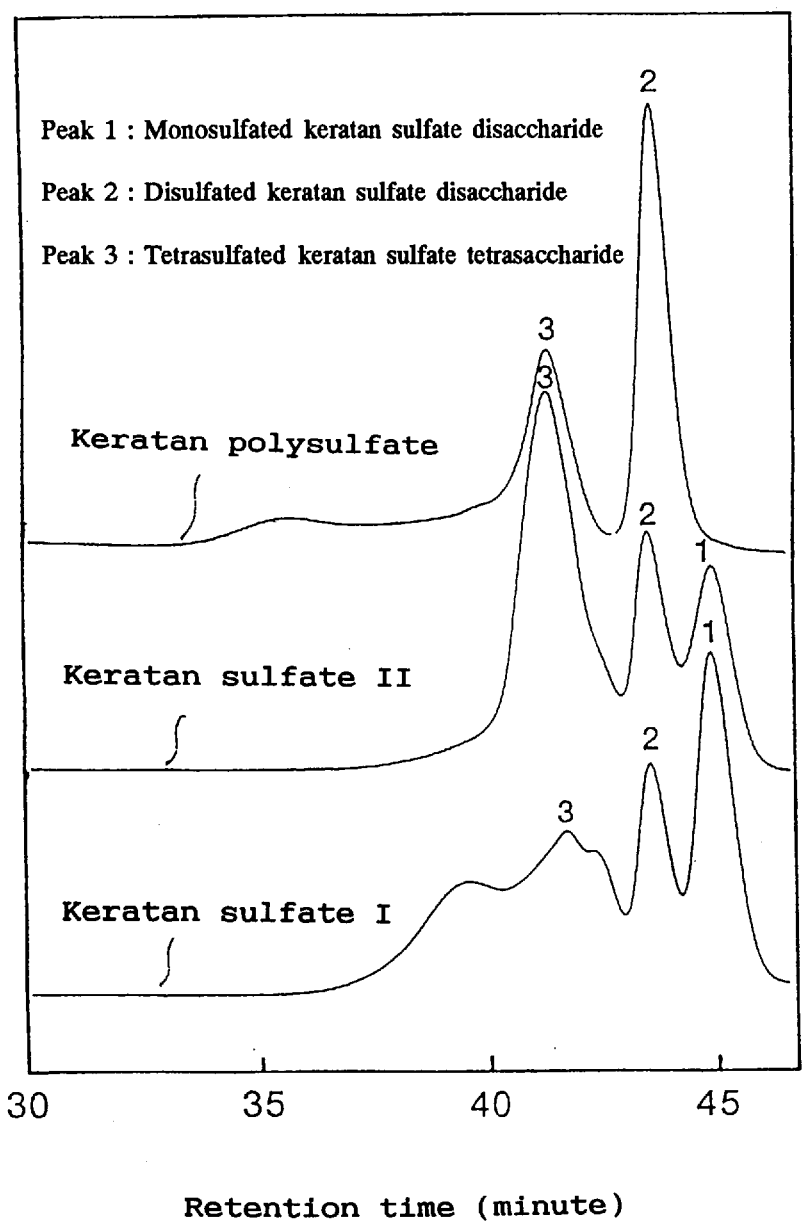
FIG. 1 is a diagram showing substrate specificity of the enzyme of the present invention.

The present invention will be further described with reference to the following examples. The enzyme activity was determined by the Park-Johnson method.

EXAMPLE 1

Isolation of *Bacillus circulans* KsT202

A small amount of the soil was added to 5 ml of a liquid medium containing a nitrogen source, inorganic salts, and keratan sulfate, and cultured with shaking at 45° C. for three days. After the cultivation, 10 µl each of the supernatant of the cultured medium and the liquid medium (control) was spotted on a filter paper. After air-drying, the filter paper was soaked in a toluidine blue solution and washed adequately with a dilute acetic acid solution, and the color on the spotted site of the supernatant of the cultured medium was compared with that of the control. Since toluidine blue combines with keratan sulfate to develop a blue color, it was confirmed that a keratan sulfate assimilative microorganism existed in the sample developing a less color than the control. The keratan sulfate assimilative microorganism was pure-isolated by a conventional method from the culture solution using a plate medium (e.g., Heart infusion Agar).

Through a variety of microorganisms pure-isolated were examined for the assimilation of keratan sulfate using a liquid medium in the same manner as in the above, the desired keratan sulfate assimilative microorganism was obtained. The following are the morphological properties, growth properties, and physiological properties of this strain.

Microbiological properties:

| (A) Morphological properties | |
|---|---|
| Gram stain | negative |
| cell shape | rods |
| | (0.3–0.4 µm × 1.9–3.3 µm) |
| spore shape | oval |
| sporangium swelling | positive |
| parasporal crystals | negative |
| motility | positive |
| (B) Growth properties | |
| aerobic growth | positive |
| anaerobic growth | negative |
| growth temperature | |
| at 30° C. | positive |
| at 40° C. | positive |
| at 45° C. | positive |
| at 50° C. | negative |
| growth in the presence of lysozyme (0.001%) | positive |
| growth in the presence of NaCl | positive |
| at concentration of 2% | |
| at concentration of 5% | negative |
| at concentration of 7% | negative |
| growth at pH 6.8 (nutrient medium) | positive |
| growth at pH 5.7 (Sabouraud dextrose medium) | negative |
| requirement for NaCl and KCl | negative |
| (C) Physiological and other properties | |
| catalase | positive |
| V-P test | negative |
| pH in V-P medium | below 6.0 |
| production of acid | |
| from D-glucose | positive |
| from L-arabinose | positive |
| from D-xylose | positive |
| from D-mannitol | negative |
| from D-mannose | positive |
| from sorbitol | negative |
| production of gas from D-glucose | negative |
| formation of indole | negative |
| hydrolysis of casein | negative |
| hydrolysis of starch | positive |
| degradation of tyrosine | negative |
| deamination of phenylalanine | negative |
| reduction of nitrate | negative |
| utilization of citrate | negative |
| utilization of propionate | negative |
| assimilation of heparin | negative |
| assimilation of heparan sulfate | negative |
| assimilation of chondroitin sulfate | positive |
| assimilation of keratosulfate | positive |
| content of guanine + cytosine (G + C) | 51.7 mole % |
| main isoprenoid quinone | menaquinone-7 |
| diaminopimelic acid (DAP) in cell wall peptidoglycan | meso-DAP |

The taxonomical investigation of the strain KsT202 having the microbiological properties above was done according to Bergey's Manual of Systematic Bacteriology, the first edition, Vol. 2 (1986). The present microorganism was recognized to be a strain belonging to the genus Bacillus based on the fact that the microorganism was an aerobic gram negative rod-shaped microorganism with motility and formed spores, the main isoprenoid quinone thereof was menaquinone-7, and it contained meso-diaminopimelic acid in the peptidoglycan of cell wall. Further, as the result of the investigation of other properties thereof, the microorganism has been identified as *Bacillus circulans*. To date, none of the known *Bacillus circulans* has been reported to assimilate keratan sulfate, and therefore, the present strain is a novel and can be distinguished from the known ones in this regard.

The *Bacillus circulans* KsT202 has been deposited as the international deposition in National Institute of Bioscience and Human-Technology of Agency of Industrial Science & Technology under accession number FERM BP-5285.

EXAMPLE 2

Extraction of Keratan Sulfate Hydrolase from *Bacillus circulans* KsT202

(1) Disrupting or lysing of the microbial cells

The cell extract of *Bacillus circulans* KsT202 was prepared by a variety of the disrupting methods or lysing methods for microbial cells described below using a microbial cell suspension which was obtained by suspending 1 g each of the freezed microbial cells in 3 ml of the phosphate-buffered saline (PBS: 100 mM $KH_2PO_4$, 0.155M NaCl, pH 7.2), and the extraction efficiency of the enzyme of the present invention was determined.

(Extraction conditions)

(1) Ultrasonic-disrupting method: treat using an ultrasonic generator (Insonator 201M; Kubota Corporation.) at 20 kHz of frequency with 40 W of power for 30 seconds was done in an ice-water bath six times at one-minute intervals.

(2) Freezing and thawing method: the freezed microbial cells were thawed by maintaining at 37° C. for 30 minutes.

(3) Lysing method with surfactant: Brij-35 (Nacalai Tesque) was added to the microbial cell suspension to a final concentration of 5% and it was maintained at 37° C. for 30 minutes.

(4) Lysing method with enzyme: lysozyme (Seikagaku Corporation) was added to the microbial cell suspension to a final concentration of 100 μg/ml and it was maintained at 37° C. for 30 minutes.

The amount of protein and the activity of keratan sulfate hydrolase in the microbial cells disrupted or the microbial cells lyzed obtained above were determined. Table 1 shows total activity, activity per unit of protein, and enzyme recovery. The amount of protein is shown as determined values by the Lowry method using serum albumin as the standard. The recovery is represented as relative values when defining the total activity in the disrupted microbial cells obtained by the ultrasonic-disrupting method as 100. The present enzyme was efficiently extracted from the microbial cells by any of the methods.

TABLE 1

| Method | Total activity (Units) | Specific activity (U/mg protein) | Recovery (%) |
|---|---|---|---|
| Ultrasonic-disrupting | 3.0 | 0.053 | 100.0 |
| Freezing and thawing | 3.1 | 0.074 | 103.4 |
| Lysing with surfactant | 4.2 | 0.043 | 141.1 |
| Lysing with enzyme | 3.8 | 0.091 | 127.5 |

(2) Effect of Deoxyribonuclease on Extraction of Keratan Sulfate Hydrolase from Lyzed Solution with Enzyme In the preparation of the extract of microbial cells by the lysing method with enzyme using lysozyme, deoxyribonuclease I (DNase I; Funakoshi) was added to determine the extraction efficiency of the present enzyme. To the microbial cell suspension (0.2 g/ml-PBS) which was obtained by suspending the freezed microbial cells in the phosphate-buffered saline (PBS: 100 mM $KH_2PO_4$, 0.155M NaCl, pH 7.2), lysozyme was added at a concentration of 50 μg/ml, and the suspension was maintained at 37° C. for 30 minutes. To the lysate, DNase I was added to concentrations from 0.2 to 26 μg/ml, and was reacted at 37° C. for 30 minutes. After the reaction, each of the reaction liquids was centrifuged to remove the residue of the microbial cells, and the quantities of the supernatants and the enzym activities were determined. Table 2 shows the results. The extraction efficiency is represented as relative values when defining the total activity without adding DNase I as 100. These results have proved elevation in the extraction efficiency by the addition of DNase to the lysate.

TABLE 2

| DNase I concentration (μg/ml) | Supernatant quantity after centrifugation (ml) | Total activity (Units) | Extraction efficiency (%) |
|---|---|---|---|
| 0.0 | 1.0 | 0.69 | 100.0 |
| 0.2 | 1.4 | 1.23 | 177.0 |
| 2.0 | 1.5 | 1.31 | 189.7 |
| 4.0 | 1.6 | 1.63 | 236.5 |
| 8.0 | 1.6 | 1.74 | 252.3 |
| 18.0 | 1.6 | 1.54 | 222.6 |
| 26.0 | 1.6 | 1.63 | 236.5 |

(3) Re-extraction of Keratan Sulfate Hydrolase from Residue of Microbial Cells

In order to investigate the extraction efficiency, the present enzyme was re-extracted from the residue of the microbial cells. The extract of the microbial cells was prepared using the suspension of 8 g of the frozen microbial cells in 32 ml of PBS by the freezing and thawing method (see Example (1)) or the lysing method with enzyme (combined use of DNase, see (2)). The extract of the microbial cells was separated into the supernatant and residue of the microbial cells by centrifugation (10,000 rpm, 40 minutes).

The residue of the microbial cells obtained by the freezing and thawing method was maintained at −20° C. for 16 hours (froze again), and it was thawed under the same conditions as in the above to re-extract. While the residue of the microbial cells obtained by the lysing method with enzyme was suspended in the same quantity of PBS as in the above to re-extract. In each of the cases, the re-extraction was repeated three times, and the enzym activity of keratan sulfate hydrolase in the supernatant of each of the extracts (from the first extraction and the three re-extractions) was determined. Table 3 shows the results.

TABLE 3

| Extraction times | Freezing and thawing method (Units) (%) | Lysing method with enzyme (Units) (%) |
|---|---|---|
| 1 | 19.8 (58.9) | 30.6 (71.7) |
| 2 | 6.8 (20.2) | 11.0 (25.8) |
| 3 | 6.1 (18.2) | 1.1 (2.5) |
| 4 | 0.9 (2.7) | 0.0 (0.0) |
| Total activity | 33.6 (100) | 42.7 (100) |

The recovery resulted in 97% or more by three times of the extraction in the freezing and thawing method or by twice of the extraction in the lysing method with enzyme. And the quantity of the enzyme obtained by the lysing method with enzyme was 27% larger than that obtained by the freezing and thawing method.

EXAMPLE 3

50 ml of a medium (pH 7.5) containing 1.0% of peptone (Kyokuto Seiyaku Kogyo), 0.75% of beer yeast extract (Nippon Seiyaku), 0.25% of fish meat extract (Kyokuto Seiyaku Kogyo), 0.5% of keratan polysulfate prepared from cartilage of sharks (Seikagaku Corporation), 0.5% of $K_2HPO_4$, 0.02% of $MgSO_4 \cdot 7H_2O$, and 0.1% of NaCl was put into a shouldered flask with a capacity of 0.5-L, autoclaved at 121° C. for 20 minutes, inoculated aseptically with a platinum loop of *Bacillus circulans* KsT202, and cultured at 37° C. for 16 hours with shaking (120 stroke/minute, 7 cm amplitude).

After the cultivation, the microbial cells were harvested with a centrifuge and disrupted with a ultrasonic-disrupter. The potency of keratan sulfate hydrolase in the disruption liquid was determined by the above-mentioned method to give 45 milliunits per liter of the cultured medium.

EXAMPLE 4

20 L of a medium (pH 7.5) containing 1.0% of peptone (Kyokuto Seiyaku Kogyo), 0.75% of beer yeast extract (Nippon Seiyaku), 0.25% of fish meat extract (Kyokuto Seiyaku Kogyo), 0.5% of keratan polysulfate prepared from cartilage of sharks (Seikagaku Corporation), 0.5% of $K_2HPO_4$, 0.02% of $MgSO_4 \cdot 7H_2O$, 0.1% of NaCl, and 0.0015% of an antiforming agent, Adekanol LG109 (Asahi Denka Kogyo) was put into a jar fermenter with a capacity of 30-L, autoclaved at 121° C. for 20 minutes, inoculated aseptically with 0.6 L (3%) of the cultured solution of the KsT202 strain which was previously cultured with shaking in the medium described in Example 3 at 37° C. for 16 hours, and cultured at 37° C. for 8 hours with aeration (1 vvm) and stirring (300 rpm). 20 L of the culture solution was treated with a continuous centrifuge to obtain 170 g on wet basis of the microbial cells.

The potency of keratan sulfate hydrolase included in the microbial cells was determined by ultrasonic-disruption of a part of the microbial cells to give 5.1 units per gram on wet basis. The residue of the microbial cells was freezed to preserve.

EXAMPLE 5

20 L of a medium (pH 8.0) containing 1.5% of peptone (Kyokuto Seiyaku Kogyo), 0.75% of beer yeast extract (Nippon Seiyaku), 0.75% of keratan polysulfate prepared from cartilage of sharks (Seikagaku Corporation), 0.5% of $K_2HPO_4$, 0.02% of $MgSO_4 \cdot 7H_2O$, 0.5% of NaCl, and 0.0015% of an antiforming agent, Adekanol LG109 (Asahi Denka Kogyo) was put into a jar fermenter with a capacity of 30-L, autoclaved at 121° C. for 20 minutes, inoculated aseptically with 1 L (5%) of the cultured solution of the strain of KsT202 which was previously cultured with shaking in the same medium at 37° C. for 16 hours, and cultured at 45° C. for 24 hours with aeration (1 vvm) and stirring (300 rpm). 20 L of the cultured solution was treated with a continuous centrifuge to remove the microbial cells and give approximately 20 L of the extracellular fluid.

The potency of keratan sulfate hydrolase included in the extracellular fluid was 11.6 milliunits per milliliter.

EXAMPLE 6

To 5 g of the freezed and preserved microbial cells obtained in Example 4, 25 ml of the 10 mM phosphate-buffered saline (pH 7.2) was added to give a microbial cell suspension, and it was stirred slowly at 37° C. for 60 minutes to extract the enzyme. After the extract was centrifuged, ammonium sulfate was added to the supernatant to 30% saturation, and the deposited precipitate was removed by centrifugation. Then further ammonium sulfate was added to 60% saturation, and the deposited precipitate was recovered by centrifugation.

After this precipitate was dissolved in approximately 20 ml of 10 mM tris-hydrochloride buffer (pH 7.2), it was dialyzed against 5 L of the same buffer at 4° C. overnight. After confirming the conductivity of the solution to be not more than 1 mS/cm, the solution was passed through a DEAE-cellulose·DE52 (Whatman) column (2.4×14 cm) which was previously equilibrated with the 10 mM tris-hydrochloride buffer (pH 7.2) to allow the enzyme to be adsorbed. After the column was washed with 100 ml of the same buffer, the enzyme was eluted with a linear increasing concentration of sodium chloride from zero to 1M in the same buffer.

To the eluted active fraction, sodium chloride was added to bring the concentration to 4M, and the fraction was passed through a Phenyl-Sepharose (Pharmacia) column (1.5×14 cm) which was equilibrated with the tris-hydrochloride buffer (pH 7.2) containing 4M sodium chloride to allow the enzyme to be adsorbed, and the enzyme was eluted with a linear decreasing concentration of sodium chloride from 4M to zero in the same buffer, and 74 ml of the purified enzyme was obtained. The enzyme obtained was 14 units, the specific activity thereof was 1.22 unit/mg (calculated in terms of the weight of bovine serum albumin), the recovery thereof from the extract of the microbial cells was 55%, and the specific activity increased approximately 60-fold. The purified enzyme did not contain contaminating enzymes such as glycosidases.

EXAMPLE 7

To the extracellular fluid obtained in Example 5, ammonium sulfate was added to 70% saturation, and the deposited precipitate was recovered by centrifugation and dissolved in 2.5 L of the 10 mM tris-acetate buffer (pH 7.5). To this solution, ammonium sulfate was added to 35% saturation, the deposited precipitate was removed by centrifugation, further ammonium sulfate was added to 55% saturation, and the deposited precipitate was recovered by centrifugation.

The precipitate was dissolved in 2.5 L of the 10 mM tris-acetate buffer (pH 7.5), and passed through a DEAE-cellulose·DE52 (Whatman) column (5.2×24 cm) which was previously equilibrated with the same buffer to allow the enzyme to be adsorbed. After the column was washed with 1.5 L of the same buffer, the enzyme was eluted with a linear increasing concentration of sodium chloride from zero to 0.3M in the same buffer.

The active fraction was collected, and ammonium sulfate was added thererto to 55% saturation, and then the precipitate was recovered by centrifugation and dissolved in a small amount of 10 mM tris-acetate buffer (pH 7.5). Then the solution was loaded onto a Sephacryl S-300 (Pharmacia) column (3.4×110 cm), and subjected to gel filtration with the 50 mM tris-acetate buffer (pH 7.5) containing 0.5M sodium chloride.

The active fraction was concentrated by ultrafiltration using UK-10 membrane (Advantec Toyo) and dialyzed against an approximately 100-fold amount of the 10 mM tris-acetate buffer (pH 7.5). The inside solution was passed through a DEAE-Toyopearl (Tosoh Corporation) column (2.2×15 cm) which was previously equilibrated with the same buffer to allow the enzyme to be adsorbed. Then the column was washed with 150 ml of the same buffer containing 0.1M sodium chloride, and the enzyme was eluted with a linear increasing concentration of sodium chloride from 0.1 to 0.2M in the same buffer.

The active fraction was concentrated by ultrafiltration, loaded onto a Sephacryl S-300 column (2.2×101 cm), and subjected to gel filtration.

After sodium chloride was added to the active fraction to a concentration of 4M, the solution was passed through a Phenyl-Sepharose (Pharmacia) column (1.6×15 cm) which was equilibrated with the tris-acetate buffer (pH 7.5) containing 4M sodium chloride to allow the enzyme to be adsorbed, and then the enzyme was eluted with a linear decreasing concentration of sodium chloride from 4M to zero in the same buffer. The enzyme obtained was 29 units, the specific activity thereof was 2.09 unit/mg (calculated in terms of the weight of bovine serum albumin), the recovery thereof from the extracellular fluid was 12.5%, and the specific activity increased approximately 180-fold. The purified enzyme did not contain contaminating enzymes such as glycosidases.

EXAMPLE 8

Using the keratan sulfate hydrolase obtained in Example 7 above, the substrate specificity, optimum reaction pH, pH stability, optimum reaction temperature, thermostability, and molecular weight of the keratan sulfate hydrolase of the present invention were evaluated by the following methods.
(1) Substrate specificity It was experimented that the keratan sulfate hydrolase obtained in Example 7 above was allowed to act on keratan sulfate I, keratan sulfate II, and keratan polysulfate, respectively. FIG. 1 shows a gel filtration chromatogram of the hydrolyzates obtained thereby. The result indicates that the main hydrolyzate obtained by allowing the keratan sulfate hydrolase of the present invention to act on keratan sulfate I, keratan sulfate II, and keratan polysulfate includes sulfated keratan sulfate disaccharide and sulfated keratan sulfate tetrasaccharide.

Further, it was experimented that the keratan sulfate hydrolase obtained in Example 7 was allowed to act on desulfated keratan sulfate in the same conditions. It was confirmed that the keratan sulfate hydrolase obtained in Example 7 does not act on the desulfated keratan sulfate and requires a sulfate group in the sugar chain at the action site. Furthermore, the same experiment was performed on glycosaminoglycan other than keratan sulfate, and the keratan sulfate hydrolase of the present invention did not act on them.

Figure 2:
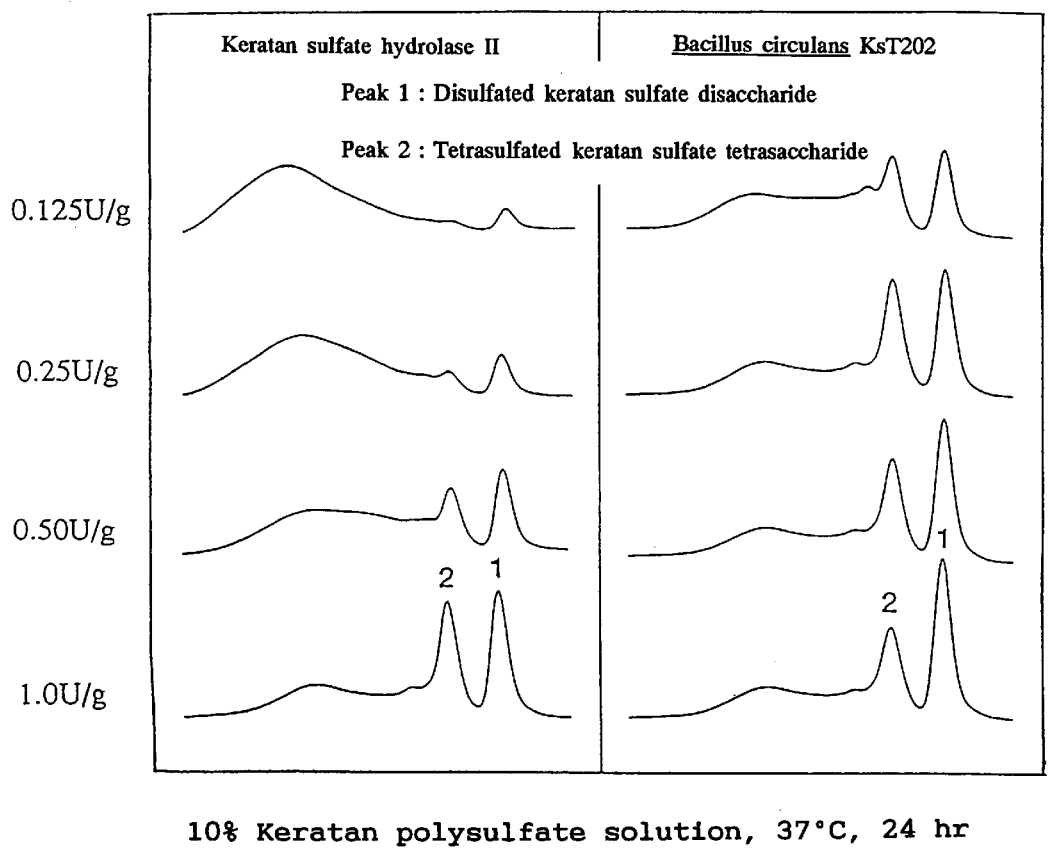
FIG. 2 is a diagram showing substrate specificity (reactivity) of the enzyme of the present invention and keratanase II on keratan polysulfate (10%).

Additionally, it was experimented that a variety of the amounts shown in FIG. 2 of the keratan sulfate hydrolase obtained in Example 7 and the known keratan sulfate hydrolase II were allowed to act on a keratan polysulfate solution of high concentration (10%) at 37° C. for 24 hours. FIG. 2 shows a gel filtration chromatogram of the lysates obtained thereby. The result reveals that even an extremely small amount of the keratan sulfate hydrolase of the present invention sufficiently acts on keratan polysulfate in a solution of high concentration (10%).

(2) Optimum reaction pH

Figure 3:
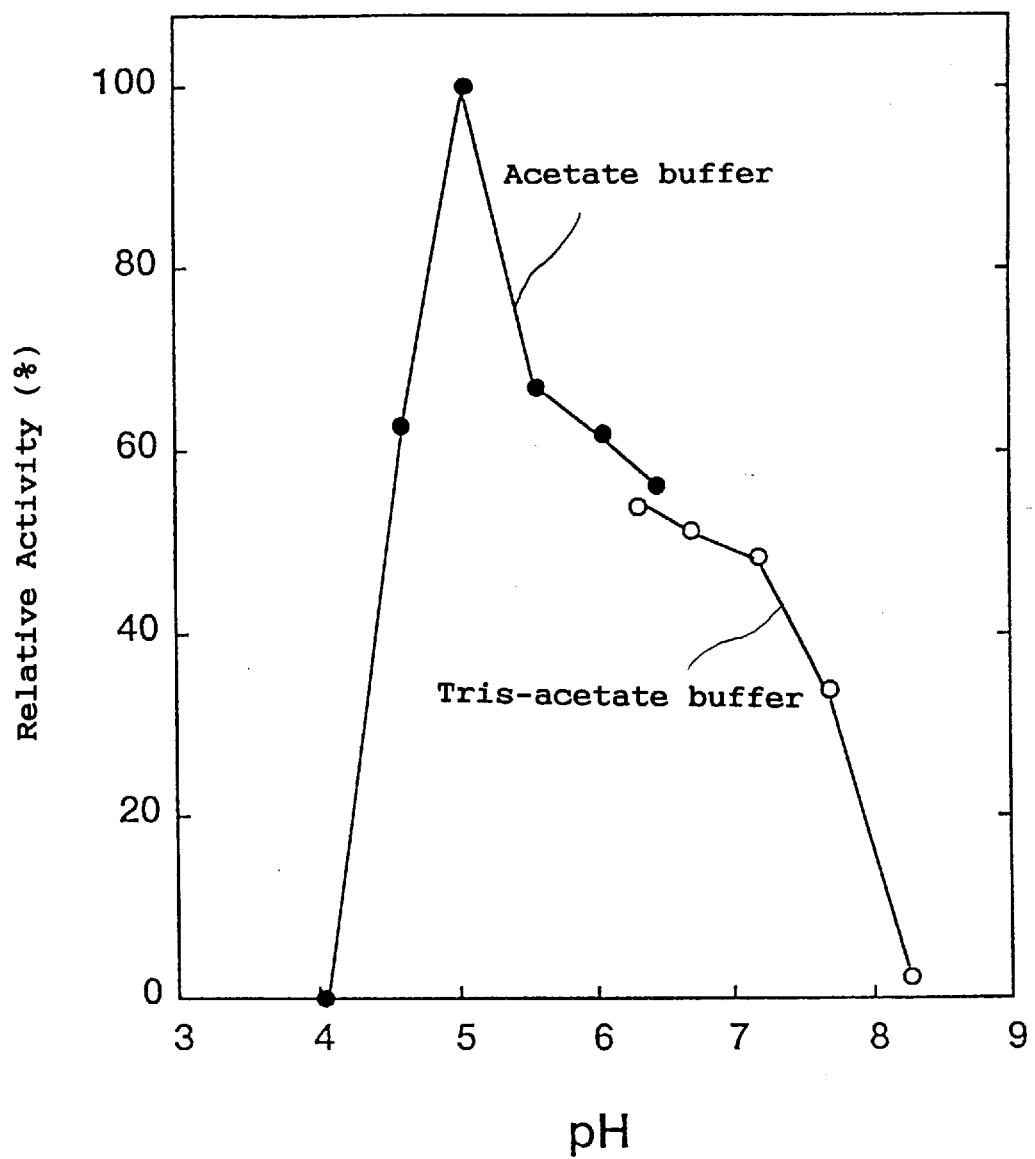
FIG. 3 is a diagram showing an optimum reaction pH of the enzyme of the present invention.

The activity of the keratan sulfate hydrolase obtained in Example 7 was determined in the 0.1M acetate buffer and 10 mM tris-acetate buffer at varying pH at 37° C. FIG. 3 shows the results. The results indicate that the optimum pH of the keratan sulfate hydrolase is from 4.5 to 6.

(3) pH Stability

Figure 4:
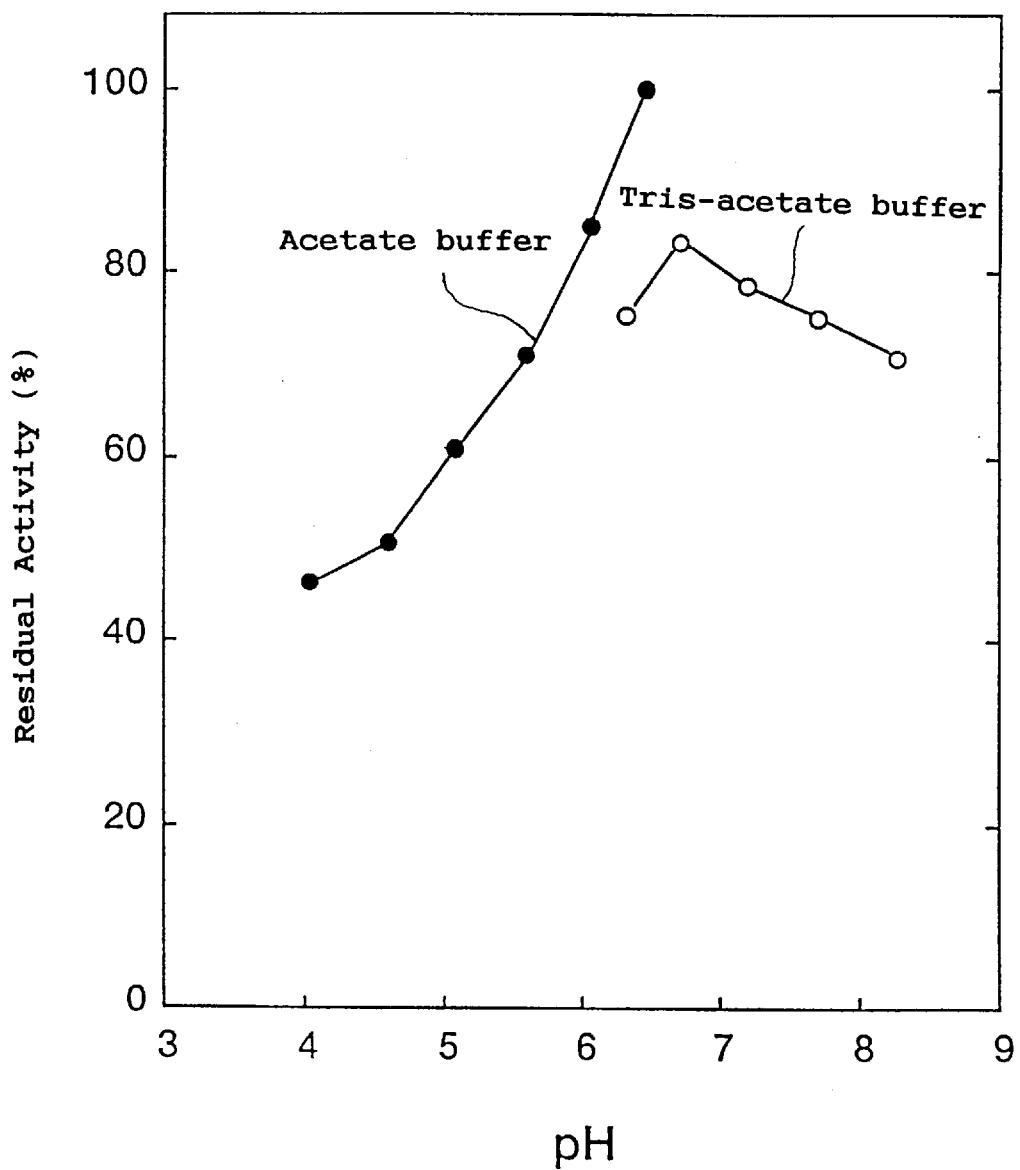
FIG. 4 is a diagram showing a pH stability of the enzyme of the present invention.

The residual activity of the keratan sulfate hydrolase obtained in Example 7 was determined after standing in the 0.1M acetate buffer and 10 mM tris-acetate buffer at varying pH at 37° C. for one hour. FIG. 4 shows the results. The results indicate that the keratan sulfate hydrolase of the present invention is stable around 6 to 7.

(4) Optimum reaction temperature

Figure 5:
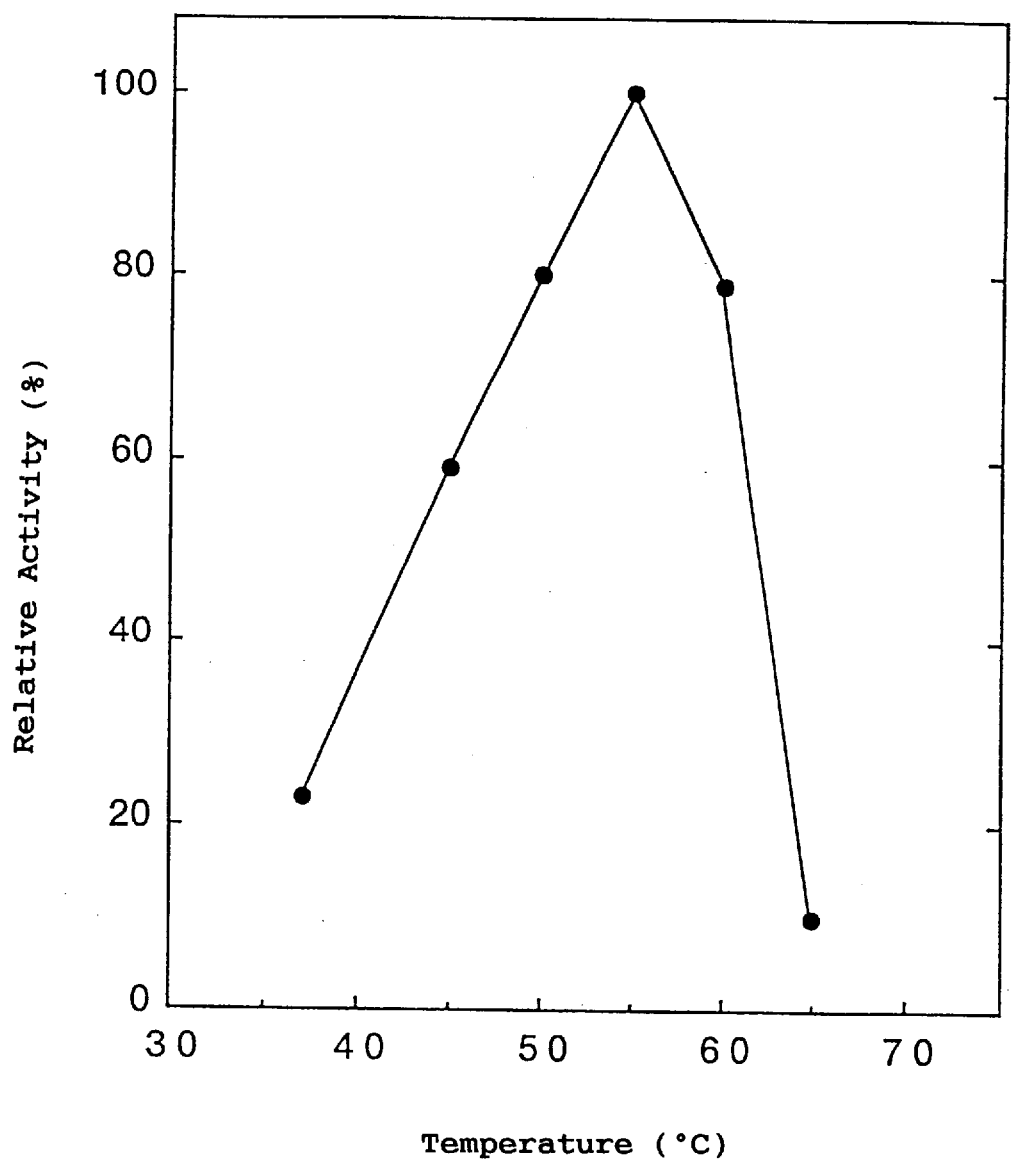
FIG. 5 is a diagram showing an optimum reaction temperature of the enzyme of the present invention.

The activity of the keratan sulfate hydrolase obtained in Example 7 was determined when it was reacted in the 0.1M acetate buffer (pH 6.0) under varying temperature condition from 37° to 65° C. for 10 minutes. FIG. 5 shows the results. The results indicate that the optimum reaction temperature of the keratan sulfate hydrolase of the present invention is from 50° to 60° C.

(5) Thermostability

Figure 6:
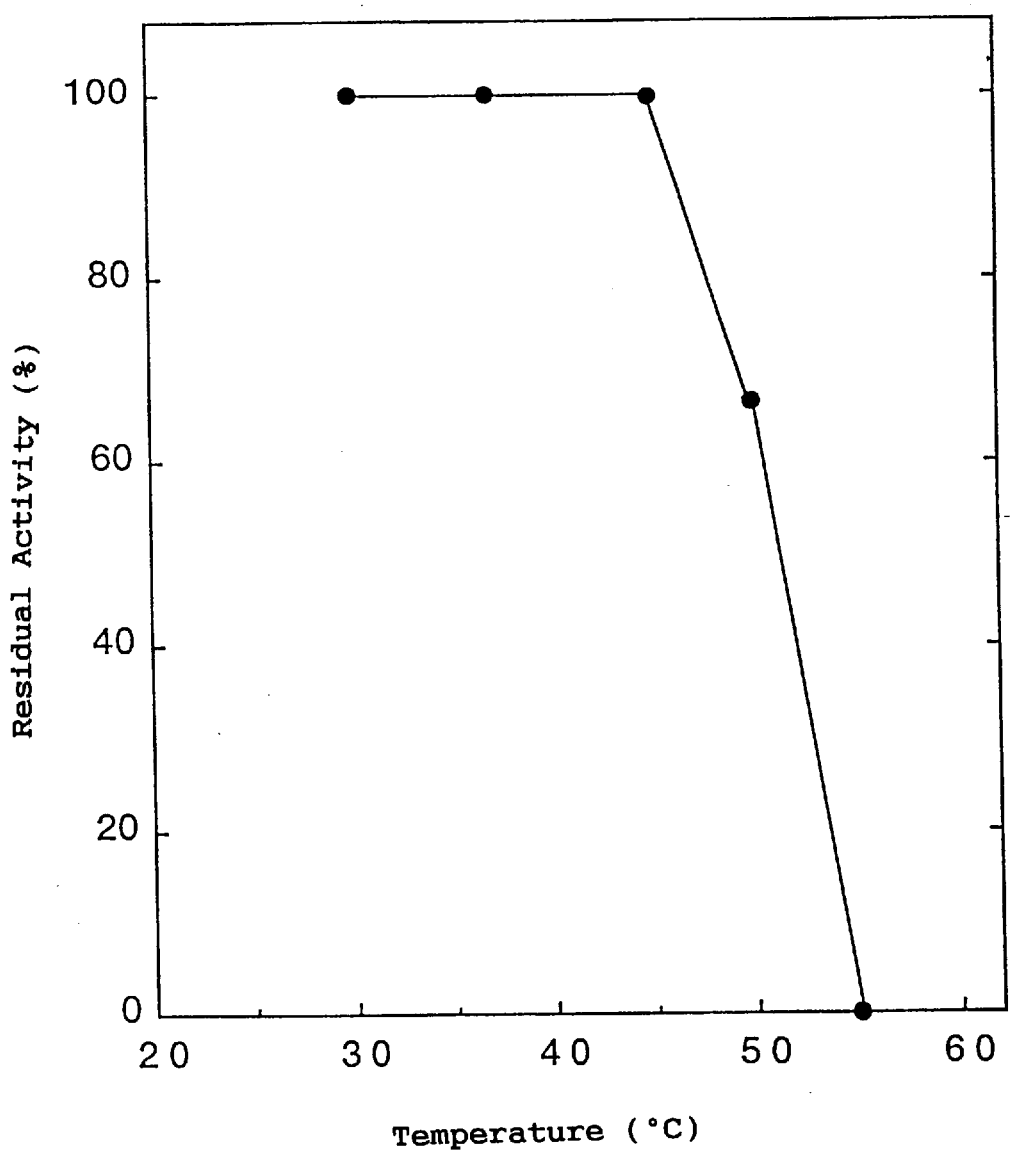
FIG. 6 is a diagram showing a thermostability of the enzyme of the present invention.

The residual activity of the keratan sulfate hydrolase obtained in Example 7 was determined after standing in the 0.1M acetate buffer (pH 6.0) under varying temperature condition from 30° to 55° C. for one hour. FIG. 6 shows the results. The results indicate that the keratan sulfate hydrolase of the present invention is not deactivated at 45° C. and has 65% of the residual activity at 50° C.

(6) Molecular weight

Figure 7:
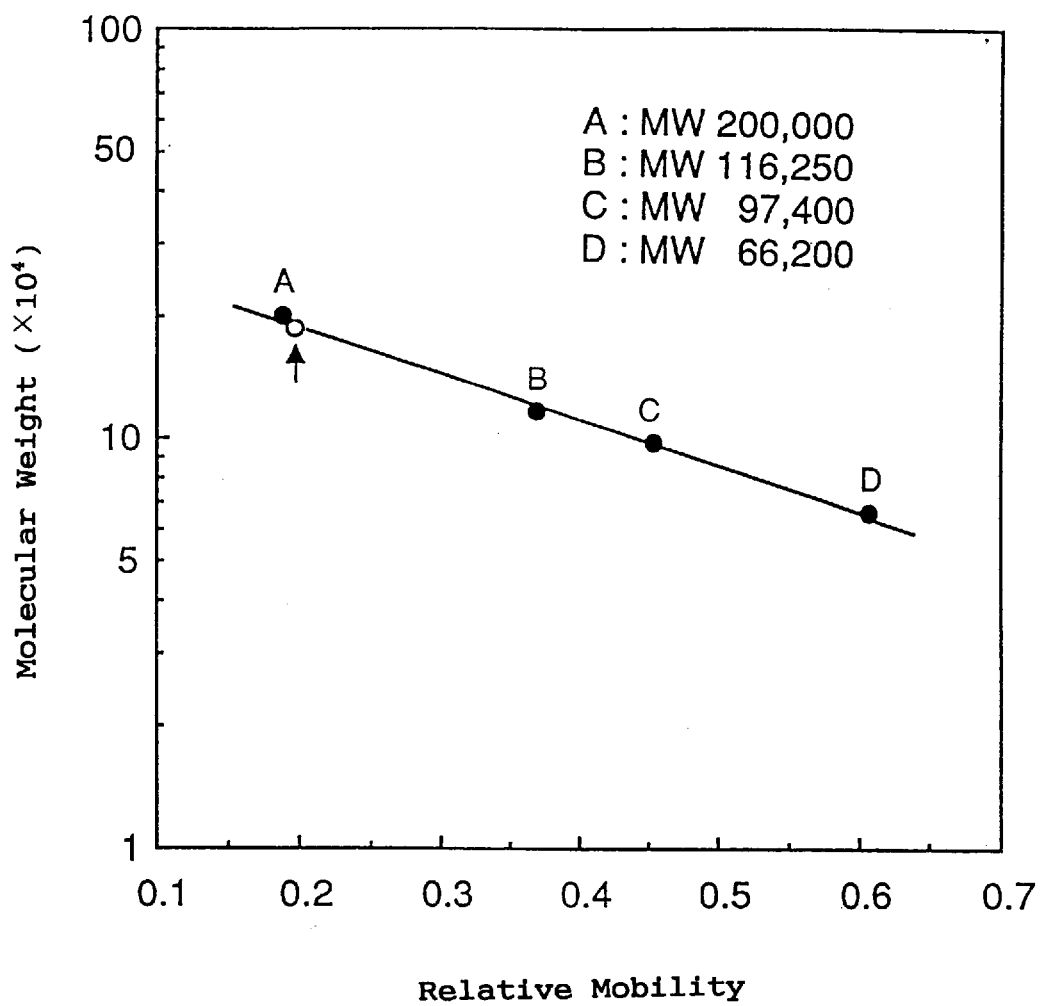
FIG. 7 is a diagram showing a molecular weight of the enzyme of the present invention.

The keratan sulfate hydrolase obtained in Example 7 was electrophoresed by SDS-polyacrylamide gel electrophoresis (in the gel concentration of 7%) under the reducing and nonreducing conditions. As the result a single band having the same mobility was shown under the both conditions. FIG. 7 shows the mobility obtained with the calibration curve of the standard protein. In FIG. 7, "o" shows the plot of the determination result of the keratan sulfate hydrolase obtained in Example 7. From the result, the molecular weight of the keratan sulfate hydrolase of the present invention was calculated to approximately 200,000 dalton.

Industrial Applicability

The present invention has provided a novel keratan sulfate hydrolase of endo-β-N-acetylglucosaminidase type having high thermostability and a novel strain of *Bacillus circulans* producing the same.

What is claimed is:

1. An isolated keratan sulfate hydrolase which has the following physicochemical properties:
   (a) catalyzing the hydrolysis of the N-acetylglucosaminidic linkage of keratan sulfate;
   (b) acting on keratan sulfate I, keratan sulfate II, and keratan polysulfate and producing sulfated keratan sulfate disaccharide and sulfated keratan sulfate tetrasaccharide as main hydrolyzates;
   (c) an optimum reaction pH from 4.5 to 6 in a 0.1M acetate buffer or 10 mM tris-acetate buffer at 37° C.;
   (d) stable in the pH range of from 6 to 7 when the hydrolase is maintained in a 0.1M acetate buffer or 10 mM tris-acetate buffer at 37° C. for one hour;
   (e) an optimum reaction temperature from 50° to 60° C. when the hydrolase reacts in a 0.1M acetate buffer, pH 6.0, for 10 minutes;
   (f) stable in the temperature range of 45 ° C. or below when the hydrolase is maintained in a 0.1M acetate buffer, pH 6.0, for one hour; and
   (g) obtainable from *Bacillus circulans*.

2. The keratan sulfate hydrolase as defined in claim 1, wherein said *Bacillus circulans* is *Bacillus circulans* KsT202 with the accession number FERM BP-5285.

3. A method for producing a keratan sulfate hydrolase, comprising the steps of:
   producing a keratan sulfate hydrolase by culturing in a medium a strain of *Bacillus circulans* having the ability to produce the keratan sulfate hydrolase, said keratan sulfate hydrolase having the following physicochemical properties:
   (a) catalyzing the hydrolysis of the N-acetylglucosaminidic linkage of keratan sulfate;
   (b) acting on keratan sulfate I, keratan sulfate II, and keratan polysulfate and producing sulfated keratan sulfate disaccharide and sulfated keratan sulfate tetrasaccharide as main hydrolyzates;
   (c) an optimum reaction pH from 4.5 to 6 in a 0.1M acetate buffer or 10 mM tris-acetate buffer at 37° C.;
   (d) stable in the pH range of from 6 to 7 when the hydrolase is maintained in a 0.1M acetate buffer or 10 mM tris-acetate buffer at 37° C. for one hour;
   (e) an optimum reaction temperature from 50° to 60° C. when the hydrolase reacts in a 0.1M acetate buffer, pH 6.0, for 10 minutes; and
   (f) stable in the temperature range of 45° C. or below when the hydrolase is maintained in a 0.1M acetate buffer, pH 6.0, for one hour; and
   recovering the keratan sulfate hydrolase from the medium and/or a cell extract of the cultured microorganism.

4. The method for producing a keratan sulfate hydrolase as defined in claim 3, wherein the microorganism belonging to *Bacillus circulans* is *Bacillus circulars* KsT202 with the accession number FERM BP-5285.

5. The method for producing a keratan sulfate hydrolase as claimed in claim 4, wherein the cell extract is obtained by lysing or disrupting microbial cells of the cultured microorganism and treating the lysed or disrupted microbial cells with deoxyribonuclease.

6. The method for producing a keratan sulfate hydrolase as claimed in claim 3, wherein the cell extract is obtained by lysing or disrupting microbial cells of the cultured microorganism and treating the lysed or disrupted microbial cells with deoxyribonuclease.

7. An isolated keratan sulfate hydrolase produced by *Bacillus circulans* KsT202 with the accession number FERM BP-5285.

8. A method for producing a keratan sulfate hydrolase, comprising the steps of:

producing a keratan sulfate hydrolase by culturing a strain of *Bacillus circulans* KsT202 with the accession number FERM BP-5285 in a medium; and recovering the keratan sulfate hydrolase from the medium and/or a cell extract of the cultured strain.

* * * * *